United States Patent [19]
Kabra

[11] Patent Number: 5,827,835
[45] Date of Patent: Oct. 27, 1998

[54] THERMALLY-GELLING EMULSIONS

[75] Inventor: Bhagwati P. Kabra, Fort Worth, Tex.

[73] Assignee: Alcon Laboratories, Inc., Fort Worth, Tex.

[21] Appl. No.: 758,787

[22] Filed: Dec. 3, 1996

Related U.S. Application Data

[63] Continuation-in-part of Ser. No. 518,289, Aug. 23, 1995, Pat. No. 5,618,800, which is a continuation-in-part of Ser. No. 298,244, Aug. 30, 1994, abandoned.

[51] Int. Cl.$^6$ ............... A61K 31/715; A01N 43/04; C08B 11/00; C08B 11/08
[52] U.S. Cl. ............... 514/57; 536/84; 536/90; 536/91; 536/95; 536/96
[58] Field of Search .............. 514/57; 536/84, 536/90, 91, 95, 96

[56] References Cited

U.S. PATENT DOCUMENTS

| | | | |
|---|---|---|---|
| 3,608,073 | 9/1971 | Phares, Jr. et al. | 424/168 |
| 4,001,211 | 1/1977 | Sarkar | 536/84 |
| 4,136,173 | 1/1979 | Pramoda et al. | 424/177 |
| 4,136,177 | 1/1979 | Lin et al. | 424/211 |
| 4,136,178 | 1/1979 | Lin et al. | 424/211 |
| 4,188,373 | 2/1980 | Krezanoski | 424/78 |
| 4,474,751 | 10/1984 | Haslam et al. | 424/78 |
| 4,474,752 | 10/1984 | Haslam et al. | 424/78 |
| 4,708,821 | 11/1987 | Shimokawa et al. | 512/12 |
| 4,798,682 | 1/1989 | Ansmann | 252/312 |
| 4,861,760 | 8/1989 | Mazuel et al. | 514/54 |
| 5,077,033 | 12/1991 | Viegas et al. | 514/668 |
| 5,124,151 | 6/1992 | Viegas et al. | 424/422 |
| 5,126,141 | 6/1992 | Henry | 424/423 |
| 5,143,731 | 9/1992 | Viegas et al. | 424/486 |
| 5,192,535 | 3/1993 | Davis et al. | 424/78.04 |
| 5,208,028 | 5/1993 | Clement et al. | 424/401 |
| 5,212,162 | 5/1993 | Missel et al. | 514/54 |
| 5,252,318 | 10/1993 | Joshi et al. | 424/78.04 |
| 5,279,660 | 1/1994 | Carlsson et al. | 106/197.1 |
| 5,296,228 | 3/1994 | Chang et al. | 424/422 |
| 5,306,501 | 4/1994 | Viegas et al. | 424/423 |
| 5,318,780 | 6/1994 | Viegas et al. | 424/427 |
| 5,358,706 | 10/1994 | Marlin et al. | 424/78.04 |
| 5,441,732 | 8/1995 | Hoeg et al. | 424/78.04 |

FOREIGN PATENT DOCUMENTS

| | | |
|---|---|---|
| 0 227 494 B1 | 7/1987 | European Pat. Off. . |
| WO 94/23750 | 10/1994 | Japan . |
| WO 89/11503 | 11/1989 | WIPO . |
| WO 92/09307 | 6/1992 | WIPO . |

OTHER PUBLICATIONS

Carlsson et al., "Thermal Gelation of Nonionic Cellulose Ethers and Iionic Surfactants in Water," *Colloids and Surfaces*, vol. 47, 147–165 (1990).

Greminger, Jr. et al., "Methylcellulose and its Derivatives," *Industrial Gums*, Academic Press, New York, Chapter XXVIII, 619–647 (1973).

Jullander, "Water Solubility of Ethyl Cellulose," *Acta Chemica Scandinavica*, 9, 1291–1295 (1955).

Safwat et al., "The Formulation–Performance Relationship of Multiple Emulsions and Ocular Activity," J. of Controlled Release, vol. 32, 259–268 (1994).

Sarkar, "Thermal Gelation Properties of Methyl and Hydroxypropyl Methylcellulose," *J. of Applied Polymer Science*, vol. 24, 1073–1087 (1979).

*Primary Examiner*—Douglas W. Robinson
*Assistant Examiner*—Everett White
*Attorney, Agent, or Firm*—Patrick M. Ryan

[57] ABSTRACT

Thermally gelling emulsion compositions which reversibly increase in either loss modulus or storage modulus, or both, upon contact with the eye, skin, mucous membrane or body cavity are disclosed. The emulsion compositions contain one or more nonionic substituted cellulose ethers and do not require a charged surfactant or a pH-sensitive polymer for such increase in loss modulus or storage modulus, or both, upon administration. In one embodiment, the compositions gel upon instillation in the eye.

13 Claims, No Drawings

THERMALLY-GELLING EMULSIONS

This application is a continuation-in-part of U.S. Ser. No. 08/518,289, filed on Aug. 23, 1995, now U.S. Pat. No. 5,618,800 which is a continuation-in-part of U.S. Ser. No. 08/298,244, filed on Aug. 30, 1994, now abandoned.

BACKGROUND OF THE INVENTION

1. Field of the Invention

The present invention relates to pharmaceutical compositions. In particular, this invention relates to emulsion compositions for delivering a pharmaceutical drug. The emulsions, which can be administrable as a drop, reversibly increase in loss modulus, storage modulus, or both, upon contact with the eye, skin, mucous membrane or a body cavity.

2. Description of Related Art

A variety of gelling drug delivery systems have been developed in an effort to prolong the contact or residence time of pharmaceutical drugs at target sites on or within the body. Drug delivery vehicles containing polysaccharide polymers which gel in response to a pH change have been proposed, such as those described in U.S. Pat. Nos. 4,136,173, 4,136,177, and 4,136,178, for example. However, compositions having an initial pH which is too low are irritating when administered to sensitive parts of the body, such as the eye.

Alternatively, drug delivery systems which gel in response to changes in ionic strength have been proposed, such as those described in European Patent No. 0 227 494 B1 and U.S. Pat. No. 4,861,760. The rates of gelation for systems which gel in response to ionic changes are dependent on the supply and diffusion of ions, and consequently are generally slower than those for thermally gelling systems because the diffusion of ions is generally a slower process than heat transfer. In addition, certain charged drug compounds cannot be used in drug delivery systems which gel in response to changes in ionic strength because they may cause premature gelation.

U.S. Pat. No. 5,212,162 discloses compositions containing both a gelling polysaccharide and a drug carrier substrate, such as finely-divided solids, colloidal particles, or soluble polymers and/or polyelectrolytes which are capable of selective adsorption or binding with drug molecules. The polysaccharide is capable of reversibly gelling based on a change in ionic strength or pH. Such factors as a change in temperature, amount and type of drug carrier substrate, and characteristics and concentrations of drugs or other adjuvants may also affect the ability of the polysaccharide to undergo a liquid-to-gel transition. The preferred polysaccharides are carrageenans.

Drug delivery systems which gel in response to temperature changes have also been proposed. For example, drug delivery systems utilizing Tetronic®, Pluronic®, or other polyols have been disclosed in U.S. Pat. Nos. 4,474,751; 4,474,752; and 4,188,373. U.S. Pat. Nos. 5,124,151; and 5,306,501 also disclose thermally gelling systems. Several disadvantages are associated with these materials. One disadvantage common to all of these thermally gelling systems is that they require a large amount of polymer (10–50 wt. %), and such large amounts of polymer can be irritating and/or toxic to the eye. Another disadvantage of some of the known thermally gelling systems is that they gel irreversibly. Such thermally irreversible gels require special precautions for product shipping and handling.

It is an inherent requirement that drug delivery systems which gel solely in response to temperature changes undergo the "sol-gel" transition at temperatures lower than physiologic temperature. It is known that methylcellulose and its hydroxyalkyl derivatives reversibly gel with increases in temperature. Generally, however, the liquid-to-gel transition temperature for cellulose polysaccharides, such as methylcellulose, occurs at temperatures well above physiologic temperature. See, for example, N. Sarkar, "Thermal Gelation Properties of Methyl and Hydroxypropyl Methylcellulose," J. of Applied Polymer Science, Vol. 24, 1073–1087 (1979).

It is known that the addition of salts to methylcellulose can adjust its liquid-to-gel transition temperature; however, the amount of salt required to adjust the transition temperature to the physiologic temperature range often results in hyperosmotic compositions which are irritating. It is also known that the gelation temperature of methylcellulose may be altered by adding hydroxypropyl substituents, but the reported change does not bring the gelation temperature any closer to physiologic temperatures. N. Sarkar, J. of Applied Polymer Science, Vol. 24, 1084 (1979).

One effort to utilize cellulose polysaccharides in liquid pharmaceutical drug delivery vehicles is disclosed in PCT Application Publication No. WO 92/09307. This reference discloses gelable carrier compositions containing a water-soluble, nonionic cellulose ether, such as ethylhydroxyethylcellulose, and a charged surfactant. The reference gels are formed by strong hydrophobic interaction between the polymer and the charged surfactant. However, charged surfactants may be toxic if delivered to sensitive parts of the body, such as the eye. Additionally, other adjuvants may detrimentally influence the polymer-charged surfactant gelation.

Various drug delivery systems employing combinations of two types of gelling polymers have also been disclosed. U.S. Pat. No. 5,077,033 discloses a thermally irreversible gel system comprising a combination of polyoxyalkylene and ionic polysaccharides. U.S. Pat. No. 5,296,228 discloses aqueous reversibly gelling polymeric solutions containing ion exchange resin particles. The polymeric component of the solution may be a pH sensitive polymer, a temperature sensitive polymer, or combinations of both pH-sensitive polymers and temperature sensitive polymers. U.S. Pat. No. 5,252,318 also discloses reversibly gelling aqueous compositions containing combinations of polymers, in this case at least one pH-sensitive reversibly gelling polymer and at least one temperature sensitive reversibly gelling polymer. One disadvantage common to systems which require pH changes in order to gel is that they must be administered at a relatively low pH, typically in the range of 2.5–4.5. Systems administered to the eye at such a relatively low pH are irritating.

U.S. Pat. No. 5,441,732 discloses reversibly gelling aqueous and oil emulsions as vehicles for delivering pharmaceutical drugs. The reference emulsions increase in viscosity in response to substantially simultaneous changes in both temperature and pH.

SUMMARY OF THE INVENTION

The present invention is directed toward non-toxic, non-irritating emulsion compositions which reversibly increase in either loss modulus or storage modulus, or both, by at least the smaller of 10 Pa or 100%, upon contact with the eye, skin, mucous membrane or a body cavity. In one embodiment, these emulsion compositions are administrable as a drop and, upon instillation in the eye, thicken to form a gel, whereby the residence or contact time of the delivered drugs with ocular tissue is increased. The emulsion compositions do not require a charged surfactant or a pH-sensitive polymer in order for such increase in loss modulus or storage modulus, or both, upon instillation. The emulsion compositions of the present invention comprise a) a nonionic cellulose ether, b) an oil, c) water, and optionally d) an emulsifying agent. The nonionic cellulose ether has a molecular weight no less than 30 kD and is substituted with one or more groups selected from alkyl, hydroxyalkyl and phenyl groups such that:

$$2.2 \leq \sum_{n=1}^{N} \{n \cdot Q(n) \cdot [MS(R_n) + MS(R_nO)] - P_N \cdot MS(R_nO)\} + Q_\phi \cdot MS(\phi) \leq 3.8$$

wherein,
  n=substituent carbon chain length;
  N=maximum value of n, $\leq 22$;
  $R_n$=alkyl group of chain length n;
  $R_nO$=alkoxy group of chain length n;
  $MS(R_n)$=MS of $R_n$;
  $MS(R_nO)$=MS of $R_nO$;
  $MS(\Phi)$=MS of phenyl groups;
  $Q(n)=0.837+0.155^*n+0.0075^*n^2 \pm 0.15$;
  $P_N$=4.4 if $N \leq 3$; 4.4–1.82 if $3<N<10$; and 1.82 if $N \geq 10$; and
  $Q_\Phi$=2.0 to 3.5.

DETAILED DESCRIPTION OF THE INVENTION

As used herein "gel" means the state of matter in which (1) G' is greater than G" (measured at a frequency in the range 0.1 to 2 Hz) when $G^*$ is greater than 10 Pa, or (2) G' is greater than or equal to twice G". G' is a storage modulus measuring the elasticity of a material, G" is a loss modulus measuring the viscous drag of a flowing liquid, and $G^*$ is a complex modulus.

As used herein "gelation temperature" means the minimum temperature at which the above definition of a gel is satisfied.

As used herein "molar substitution" or "MS" means the average number of specified substituent structural units, attached either directly or indirectly, per anhydroglucose unit comprising the cellulose backbone. The anhydroglucose unit of cellulose contains 3 pendant hydroxyl groups that can be substituted. The maximum number of substitutions is three for any substituent which is self-terminating, an example of which is an n-alkyl substituent. For substituents that are not self-terminating, such as hydroxyalkyl groups whose OH group can be further substituted, additional substituents can be concatenated and, thus, MS can exceed three.

When formulated for topical administration to the eye, the drug delivery emulsion compositions of the present invention have an osmolality of about 350 mOsm or less. Compositions having an osmolality greater than about 350 mOsm are hypertonic and can be irritating when topically administered to the eye.

When contacted with the eye, skin, mucous membrane or a body cavity, the compositions of the present invention reversibly increase in either loss modulus or storage modulus, or both, by at least the smaller of 10 Pa or 100 % in response to an increase in temperature. The compositions of the present invention comprise one or more nonionic cellulose ethers having a molecular weight no less than 30 kD. The cellulose ethers are substituted with one or more groups selected from alkyl, hydroxyalkyl and phenyl groups such that:

$$2.2 \leq \sum_{n=1}^{N} \{n \cdot Q(n) \cdot [MS(R_n) + MS(R_nO)] - P_N \cdot MS(R_nO)\} + Q_\phi \cdot MS(\phi) \leq 3.8$$

wherein,
  n=substituent carbon chain length;
  N=maximum value of n, $\leq 22$;
  $R_n$=alkyl group of chain length n;
  $R_nO$=alkoxy group of chain length n;
  $MS(R_n)$=MS of $R_n$;
  $MS(R_nO)$=MS of $R_nO$;
  $MS(\Phi)$=MS of phenyl groups;
  $Q(n)=0.837+0.155^*n+0.0075^*n^2 \pm 0.15$;
  $P_N$=4.4 if $N \leq 3$; 4.4–1.82 if $3<N<10$; and 1.82 if $N \geq 10$; and
  $Q_\Phi$=2.0 to 3.5.

Let the structure function "SF" be defined as $$SF = \sum_{n=1}^{N} \{n \cdot Q(n) \cdot [MS(R_n) + MS(R_nO)] - P_N \cdot MS(R_nO)\} + Q_\phi \cdot MS(\phi)$$

so that SF=SF {N, Q(n), $P_N$, $Q_\Phi$, MS(Rn), MS($R_nO$), MS($\Phi$)}, an expression which registers the cumulative sum over the set {n} of hydrophilic and hydrophobic interactions produced by the amount and type of each chemical functionality. Alkyl and phenyl substituents contribute to the total hydrophobicity of a cellulose ether derivative, as does the alkyl portion of any hydroxy alkyl substituent. The hydroxy and additional ether portions of hydroxy alkyl substituents contribute to the derivative's hydrophilicity. The hydrophobic or hydrophilic contribution of a particular substituent is directly proportional to its MS, and is a function of its carbon chain length. The relative contributions of the different types of substituents are represented by the coefficients, Q and P.

To determine whether a particular substituted cellulose ether satisfies the above criteria, evaluate the function for the values of the parameters describing that cellulose ether derivative, and determine whether the SF value satisfies the above inequality.

Preferably, $N \leq 4$. Also preferred are SF values such that $2.5 \leq SF \leq 3.3$. Most preferred are SF values such that $2.7 \leq SF \leq 3.3$.

The cellulose ethers useful in the present invention can be synthesized by methods known in the art, and many hydrophobically modified cellulose ether derivatives are commercially available.

The gelation of the cellulose ether-containing vehicles or formulations of the present invention occurs upon increased association of hydrophobic groups on increasing temperature. The gelation temperature of the cellulose polymer will depend upon the type, and the degree of hydrophobic and hydrophilic substitutions. For example, the gelation temperature will decrease with increase in the alkyl chain length of substituents and with increase in the molar substitution of alkyl groups. A balance of hydrophilicity is required in order to avoid precipitation.

Preferably, the cellulose ether is substituted with one or more groups selected from the group consisting of alkyl and hydroxy alkyl groups. Two examples of such cellulose ethers are methylalkylcelluloses and ethylhydroxyalkylcelluloses.

A preferred methylalkylcellulose is methylethylcellulose, wherein the methyl MS is 0.1 to 1.0, and the ethyl MS is 0.5 to 1.4. More preferred for methylethylcellulose is a methyl MS of 0.3 to 0.8 and an ethyl MS of 0.7 to 1.2. Most preferred is a methyl MS of about 0.34 and an ethyl MS of about 1.0.

Another preferred methylethylcellulose has a total MS greater than 1.6, and wherein the methyl MS is 1.3 to 2.4 and the ethyl MS is 0.1 to 0.5.

A preferred ethylhydroxyalkylcellulose is ethylhydroxyethylcellulose having an ethyl MS greater than 1 and a hydroxyethyl MS greater than 0.1. More preferred are ethylhydroxyethylcelluloses wherein the ethyl MS is 1.0 to 2.0, and the hydroxyethyl MS is 0.1 to 1.4. Most preferred are ethylhydroxyethylcelluloses wherein the ethyl MS is 1.4 to 2.0, and the hydroxyethyl MS is 0.6 to 1.4

In addition to a cellulose ether of the kind described above, the emulsion compositions of the invention also comprise oil, water, and optionally an emulsifying agent. Suitable oils include mineral oil; caprylic and capric triglycerides, such as Myritol 318; medium chain (e.g., $C_8$–$C_{12}$) triglycerides; corn oil; sesame oil; and ethyl esters of fatty acids derived from synthetic, animal or vegetable fat. In general, the amount of oil present in the emulsions of the present invention will range from about 0.1 to about 50 wt. %.

An emulsifying agent may be necessary or desired in order to improve the formation and/or stability of the emulsion. Suitable emulsifying agents include phospholipids; polyethoxylated castor oils, such as Cremaphor EL; polyoxyethylene sorbitan monooleate, such as Polysorbate 80; copolymers of polyethylene oxide and polypropylene oxide (such as Pluronics); oxyethylated tertiary octylphenol formaldehyde polymer (i.e., Tyloxapol); and tocopherosolan.

In some cases where the nonionic cellulose ether is MEC, a stable emulsion can be prepared without using a separate emulsifying agent because the surfactant-like property of MEC improves the formation and stability of the emulsion. Furthermore, the viscosity imparted to the emulsion by MEC also improves the stability of the emulsion.

In some cases where the gelation temperature is about 40° C. or less, it can be reduced to about 35° C. or less by adding adjuvants such as salts, charged surfactants and nonionic tonicity agents. However, in the case of ophthalmic formulations, the amount of adjuvant should be such that osmolality of the polymer-adjuvant formulation is not greater than 350 mOsm; the solution will become hypertonic above this value for ophthalmic applications. In general, the gelation temperature can be manipulated by the addition of electrolytes which are known to either salt in or salt out organic solutes. The ability of an electrolyte to salt out a polymer from its solution generally follows the order in the Hofmeister series. The common anions follow the order $I^-<Br^-<NO_3^-<Cl^-<tartrate<SO_4^{2-}<PO_4^{3-}$. Salts useful in the present invention include those where the anion is one or more of the following: $I^-$, $Br^-$, $NO_3^-$, $Cl^-$, tartrate, $HCO_3^-$, $CO_3^{2-}$, $SO_4^{2-}$, $PO_4^{3-}$, $B_4O_7^{2-}$, $HPO_4^{2-}$, $HPO_4^-$, citrate; and those where the cation is one or more of the following: $Na^+$, $K^+$, $Ca^{2+}$, $Al^{3+}$, $NH^{4+}$. Preferred salts for use with the compositions of the present invention are those that contain an anion selected from the group consisting of $Cl^-$, $PO_4^-$, $HCO_3^-$, $CO_3^-$, $HPO_4^-$, and $B_4O_7^{2-}$. Most preferred for use in formulations of ethylhydroxyethylcelluloses is a combination of mono- and dibasic phosphate salts such that the composition contains up to 1.5 wt. % dibasic phosphate salts and 0.5 wt. % monobasic phosphate salts.

In some cases where the gelation temperature is about 40° C. or less, it can also be reduced to about 35° C. or less by the addition of a nonionic tonicity agent, such as mannitol.

For the sake of clarity and for ease of reference in the discussion below, "pre-dosed" refers to a formulation's characteristics before instillation in the eye, or in in vitro solutions mimicking this state, and "post-dosed" refers to a formulation's characteristics after instillation in the eye, or in in vitro solutions mimicking this state.

Emulsion compositions comprising one or more pharmaceutical or therapeutic agents ("drugs") are within the scope of the present invention. Such compositions may be formulated in many ways using conventional techniques. For example, the compositions may be administered in an ungelled or weak gel state in which they are administrable as a drop from a DROPTAINER®. Alternatively, the compositions of the present invention may be administered to the eye, skin, mucous membrane or a body cavity as an extrudable gel, which, for example, could be administered out of a tube or as a gel ribbon. Upon administration to the eye, skin, mucous membrane or a body cavity, the compositions of the present invention preferably increase in either loss modulus or storage modulus, or both, by at least the smaller of 10 Pa or 100%.

In a particularly preferred embodiment, the compositions of the present invention are administered to the eye as a drop which gels upon instillation. Preferably, the gel has a $G^*$ value from 5–1,000 Pa and, more preferably from 10–200 Pa.

Remarkably strong gels can be formed by the drug delivery compositions of the present invention. In some embodiments, the gel formed is so strong that at least 50% of an initial amount of 20–50 mg of the gel remains undissolved in a static artificial tear solution after two hours. In other embodiments, the gel may persist longer than 24 hours.

In the embodiment of the present invention where the composition is administrable as a weak gel, the post-dosed gel preferably has a $G^*$ value from 50–100,000 Pa, and more preferably from 100–20,000 Pa.

Because the compositions of the present invention do not rely on any pH-sensitive adjuvant for their increase in loss or storage modulus, they are preferably formulated at a pre-dosed pH from 5.0 to 8.5, such that they are not irritating when administered to the eye.

The pre-dosed temperature of the compositions of the present invention is preferably less than 30° C., and more preferably 25° C. or less.

Additionally, drug carrier substrates ("DCS") such as those defined in U.S. Pat. No. 5,212,162 may also be utilized in the drug delivery compositions of the present invention. The entire contents of U.S. Pat. No. 5,212,162 are hereby incorporated by reference in the present specification. In addition, as used herein, "DCS" includes insoluble drug particles which may themselves act as drug carriers. Preferably, the DCS will have an average particle size less than 50 microns and will be selected from the group consisting of cation exchange resins, anion exchange resins, encapsulating microspheres, insoluble drug particles, gel particles and polymeric drug complexes.

Suitable ophthalmic agents which can be included in the compositions of the present invention and administered via the method of the present invention include, but are not limited to: glaucoma agents, such as betaxolol, pilocarpine and carbonic anhydrase inhibitors; dopaminergic agonists; post-surgical antihypertensive agents, such as para-amino clonidine (apraclonidine); anti-infectives, such as ciprofloxacin; antimicrobials, such as cephalosporins and quinolones; non-steroidal and steroidal anti-inflammatories, such as suprofen, ketorolac and tetrahydrocortisol; prostaglandins; proteins; growth factors, such as EGF; immunosuppressant agents, and anti-allergics. The cellulose ether polymers of the present invention are non-ionic and thus will not interfere with charged drug compounds. Compositions of the present invention may also include combinations of ophthalmic agents. In a formulation without the use of ophthalmic agents, the present invention may also serve to supplement tears in the prevention or treatment of dry eye.

In addition to the cellulose ether and a pharmaceutical and/or therapeutic agent, the compositions of the present invention may include other components. For example, pharmaceutically acceptable buffers, preservatives, nonionic surfactants, solubilizing agents, stabilizing agents, emollients, lubricants and/or tonicity agents may be included. Preferred preservatives for use in the compositions of the present invention which are formulated for local administration to the eye include alkylammoniumphenyl halides, such as benzalkonium chloride and benzalkonium bromide, and polyquaternium-1. Preferably in the case of ophthalmic formulations, the amount of the preservative is no more than 0.012 wt. %.

The amount of cellulose ether required will vary with the desired "post-dose" properties. Preferably, the compositions of the present invention contain from 1 to about 10 wt. %, more preferably no more than 5 wt. %, and most preferably no more than 3 wt. %, of a cellulose ether.

The following examples are presented to illustrate further various aspects of the present invention, but are not intended to limit the scope of the invention in any respect.

Example 1: Thermally Gelling Emulsion Composition 0.3 g of MEC, 0.35 g of mannitol, 0.3 g of boric acid, 0.066 g of tromethamine were combined with enough water to give 9.5 g of a composition. The MEC polymer was hydrated by stirring the solution in an ice bath for 2 hours. To this stirred composition, 0.5 g of Myritol 318 (caprylic/capric triglyceride) was added. The resulting mixture was stirred for fifteen minutes at room temperature to produce an emulsion.

We claim:

1. A non-toxic emulsion composition which reversibly increases in either loss modulus or storage modulus, or both, by at least the smaller of 10 Pa or 100% in response to an increase in temperature upon contact with the eye, skin, mucous membrane or body cavity, wherein the emulsion does not require a charged surfactant or pH-sensitive polymer for such increase in either loss modulus or storage modulus, or both, and wherein the composition comprises (a) a nonionic cellulose ether having a molecular weight no less than 30 kD and one or more substituents selected from the group consisting of alkyl, hydroxyalkyl and phenyl groups such that $$2.2 \leq \sum_{n=1}^{N} \{n \cdot Q(n) \cdot [MS(R_n) + MS(R_nO)] - P_N \cdot MS(R_nO)\} + Q_\phi \cdot MS(\phi) \leq 3.8$$

wherein,
n=substituent carbon chain length;
N=maximum value of n, $\leq 22$;
$R_n$=alkyl group of chain length n;
$R_nO$=alkoxy group of chain length n;
$MS(R_n)$=MS of $R_n$;
$MS(R_nO)$=MS of $R_nO$;
$MS(\Phi)$=MS of phenyl groups;
$Q(n)=0.837+0.155^*n+0.0075^*n^2\pm0.15$;
$P_N$=4.4 if $N \leq 3$; 4.4–1.82 if $3<N<10$; and 1.82 if $N \geq 10$; and
$Q_\Phi$=2.0 to 3.5;

provided that the nonionic cellulose ether is not a cellulose ether having only ethyl and hydroxyethyl substituents, an ethyl MS from 1.2 to 2.5 and a hydroxyethyl MS from 0.5 to 1.5, and a cloud point from 30° to 35° C. as spectrophotometrically determined for a 1.0 wt % solution of the cellulose ether in water, heated at a rate of 10° C./min; (b) an oil, c) water, and optionally d) an emulsifying agent.

2. The composition of claim 1 wherein the composition is an ophthalmic emulsion 5 composition having an osmolality$\leq 350$ mOsm.

3. The composition of claim 2 wherein $N \leq 4$.

4. The composition of claim 2 wherein either the composition's loss modulus or storage modulus, or both, increases by at least 15 Pa.

5. The composition of claim 2 wherein the composition is administrable as a drop.

6. The composition of claim 2 wherein the composition is a gel prior to instillation.

7. The composition of claim 2 wherein the composition forms a gel upon instillation in the eye.

8. The composition of claim 2 further comprising one or more drugs selected from the group consisting of anti-glaucoma agents, dopaminergic agonists, post-surgical antihypertensive agents, anti-infectives, nonsteroidal and steroidal anti-inflammatory agents, prostaglandins, proteins, growth factors, immunosuppressant agents, and anti-allergic agents.

9. The composition of claim 1 wherein the composition comprises an emulsifying agent selected from the group consisting of phospholipids; polyethoxylated castor oils; polyoxyethylene sorbitan monooleate; copolymers of polyethylene oxide and polypropylene oxide; oxyethylated tertiary octylphenol formaldehyde polymer; and tocopherosolan.

10. The composition of claim 1 wherein the oil is selected from the group consisting of mineral oil; caprylic and capric triglycerides; medium chain triglycerides; corn oil; sesame oil; and ethyl esters of fafty acids derived from a fat seleceted from the group consisting of synthetic fats; animal fats and vegetable fats.

11. The composition of claim 1 wherein the cellulose ether is selected from the group consisting of methylethylcellulose and ethylhydroxyethylcellulose.

12. A non-toxic ophthalmic emulsion composition which reversibly increases in either loss modulus or storage modulus, or both, by at least the smaller of 10 Pa or 100% in response to an increase in temperature upon instillation in the eye, wherein the composition has an osmolality$\leq 350$ mOsm and does not require a charged surfactant or pH-sensitive polymer for such increase in either loss modulus or storage modulus, or both, and wherein the composition comprises methylethylcellulose having a molecular weight no less than 30 kD, a methyl MS from 1.0 to 0.1, and an ethyl MS from 0.5 to 1.4; an oil; water; and optionally, an emulsifying agent.

13. A non-toxic ophthalmic emulsion composition which reversibly increases in either loss modulus or storage modulus, or both, by at least the smaller of 10 Pa or 100% in response to an increase in temperature upon instillation in the eye, wherein the composition has an osmolality$\leq 350$ mOsm and does not require a charged surfactant or pH-sensitive polymer for such increase in either loss modulus or storage modulus, or both, and wherein the composition comprises ethylhydroxyethylcellulose having a molecular weight no less than 30 kD, an ethyl MS from 1.0 to 2.0, and an hydroxyethyl MS from 0.1 to 1.4; an oil; water; and optionally, an emulsifying agent.

* * * * *